United States Patent
Fischer et al.

(10) Patent No.: US 9,918,726 B2
(45) Date of Patent: Mar. 20, 2018

(54) LUMEN RE-ENTRY SYSTEM AND METHOD

(71) Applicant: Cook Medical Technologies LLC, Bloomington, IN (US)

(72) Inventors: Frank Fischer, Bloomington, IN (US); Kurt Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 889 days.

(21) Appl. No.: 13/744,696

(22) Filed: Jan. 18, 2013

(65) Prior Publication Data

US 2013/0238003 A1 Sep. 12, 2013

Related U.S. Application Data

(60) Provisional application No. 61/607,754, filed on Mar. 7, 2012.

(51) Int. Cl.
*A61B 17/22* (2006.01)
*A61B 17/34* (2006.01)
*A61B 17/00* (2006.01)

(52) U.S. Cl.
CPC .......... *A61B 17/22* (2013.01); *A61B 17/3478* (2013.01); *A61B 2017/00305* (2013.01); *A61B 2017/00323* (2013.01); *A61B 2017/22044* (2013.01); *A61B 2017/22095* (2013.01)

(58) Field of Classification Search
CPC ........... A61B 2017/00305; A61B 2017/22095; A61B 17/3478; A61B 17/22; A61B 2017/22044; A61B 2017/22038; A61B 2017/22039; A61B 2017/22041; A61B 2017/22042; A61B 2017/22045; A61B 2017/22001; A61B 2017/22002; A61B 2017/2212; A61B 2017/2215; A61B 2017/2217; A61B 2017/00318; A61B 2017/00327; A61B 2017/003; A61B 17/221
USPC ......................................................... 606/159
See application file for complete search history.

(56) References Cited

U.S. PATENT DOCUMENTS

| 3,521,620 | A | | 7/1970 | Cook | |
|---|---|---|---|---|---|
| 4,886,067 | A | * | 12/1989 | Palermo | ........................ 600/434 |
| 4,909,781 | A | * | 3/1990 | Husted | ............................ 604/22 |
| 5,002,041 | A | * | 3/1991 | Chikama | ....................... 600/139 |
| 5,125,395 | A | | 6/1992 | Adair | |
| 5,378,234 | A | * | 1/1995 | Hammerslag et al. | .... 604/95.04 |
| 5,865,800 | A | | 2/1999 | Mirarchi et al. | |
| 6,126,649 | A | * | 10/2000 | VanTassel et al. | ........... 604/528 |

(Continued)

*Primary Examiner* — Eric Rosen
*Assistant Examiner* — Chima Igboko
(74) *Attorney, Agent, or Firm* — Liell & McNeil

(57) ABSTRACT

A lumen re-entry system includes a helically wound coil having open proximal and distal ends, and defining a longitudinal movement axis. The helically wound coil includes a distal segment that is relaxed relative to a proximal segment. A tip deflection wire is attached to the relaxed distal segment and coaxially disposed relative to the helically wound coil. Movement of the tip deflection wire moves the lumen re-entry system from an advancement configuration in which the open distal end of the helically wound coil is substantially aligned with the longitudinal movement axis to a deflected configuration. The lumen re-entry system also includes a puncture wire slidably received within the helically wound coil and having a distal puncture tip.

13 Claims, 3 Drawing Sheets

(56) References Cited

U.S. PATENT DOCUMENTS

| | | | |
|---|---|---|---|
| 6,231,546 B1 * | 5/2001 | Milo et al. | 604/164.13 |
| 6,533,783 B1 | 3/2003 | Tollner | |
| 6,663,577 B2 * | 12/2003 | Jen et al. | 600/585 |
| 6,726,677 B1 * | 4/2004 | Flaherty et al. | 604/528 |
| 7,850,604 B2 * | 12/2010 | Wimmer | 600/139 |
| 8,214,015 B2 * | 7/2012 | Macaulay et al. | 600/424 |
| 8,262,588 B2 * | 9/2012 | Miyata et al. | 600/585 |
| 8,337,425 B2 * | 12/2012 | Olson et al. | 600/585 |
| 8,409,236 B2 * | 4/2013 | Pillai et al. | 606/185 |
| 8,597,325 B2 * | 12/2013 | Ginn | 606/213 |
| 8,608,690 B2 * | 12/2013 | Pal | 604/103.04 |
| 8,690,891 B2 * | 4/2014 | Cowley et al. | 606/113 |
| 8,758,400 B2 * | 6/2014 | Ginn et al. | 606/213 |
| 8,852,223 B2 * | 10/2014 | Ryder et al. | 606/194 |
| 2001/0034547 A1 * | 10/2001 | Hall et al. | 623/1.11 |
| 2002/0017515 A1 * | 2/2002 | Obata et al. | 219/137 R |
| 2005/0049574 A1 * | 3/2005 | Petrick et al. | 604/525 |
| 2005/0124912 A1 * | 6/2005 | Griego et al. | 600/564 |
| 2007/0093781 A1 * | 4/2007 | Kugler et al. | 604/510 |
| 2007/0093782 A1 * | 4/2007 | Kugler et al. | 604/510 |
| 2007/0219464 A1 * | 9/2007 | Davis et al. | 600/585 |
| 2008/0243067 A1 | 10/2008 | Rottenberg et al. | |
| 2009/0043299 A1 | 2/2009 | Racz | |
| 2009/0198153 A1 | 8/2009 | Shriver | |
| 2009/0209910 A1 * | 8/2009 | Kugler et al. | 604/103.1 |
| 2009/0264902 A1 * | 10/2009 | Laufer | 606/140 |

* cited by examiner

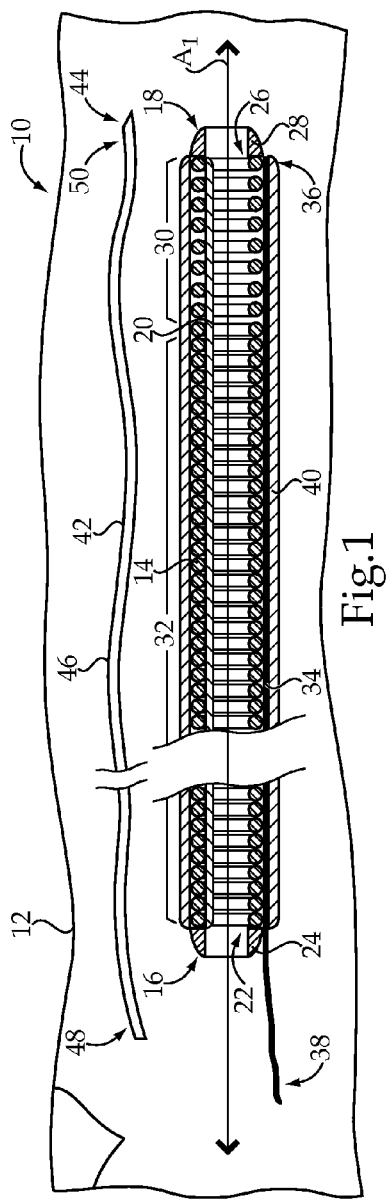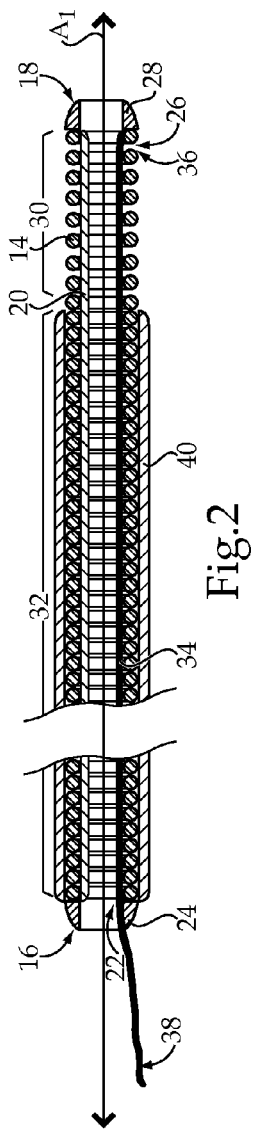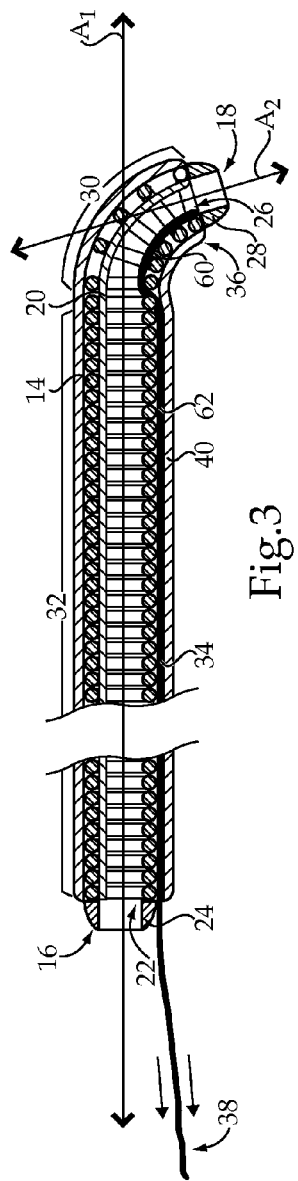

LUMEN RE-ENTRY SYSTEM AND METHOD

RELATION TO OTHER PATENT APPLICATION

This application claims priority to provisional patent application 61/607,754, filed Mar. 7, 2012, with the same title.

TECHNICAL FIELD

The present disclosure relates generally to a lumen re-entry system, and more particularly to a lumen re-entry system including a tip deflectable hollow wire guide and a puncture wire slidably received within the wire guide.

BACKGROUND

Thrombosis is the formation of a thrombus, or blood clot, within the vascular system of a patient. A blood clot typically occurs when blood hardens from a liquid to a solid. When attached to vessel walls, blood clots, and other substances, such as plaque or fat, may reduce or block blood flow downstream from the clot. Chronic total occlusion (CTO) is a complete blockage within the vascular system or, more particularly, within an arterial vessel, that obstructs blood flow. This blocked blood flow may prevent critical blood flow and oxygen from reaching certain tissues and, thus, may result in damage to the tissues. Regardless of the particular location of the clot within the vascular system, a clot or, in particular, a CTO, if left untreated, may cause serious damage and, in some cases, may become life threatening.

A wide variety of invasive and non-invasive techniques are available for treating a CTO. For example, some percutaneous techniques include the use of pharmacological agents, also referred to as thrombolytic agents, to help dissolve the clots. Other percutaneous techniques may include the use of a wire guide and/or catheter to cross the occlusion and recanalize the vessel. However, crossing a CTO using a wire guide and/or catheter may be difficult and, oftentimes, impossible, due to the hardness of the clot or occlusion. During these recanalization procedures, it is common for the wire guide to be inadvertently advanced into the subintimal space of the vessel wall. Once the wire guide has entered the subintimal space, it is often difficult to redirect the wire guide back into the lumen of the vessel.

An exemplary lumen re-entry device is described in U.S. Patent Application Publication No. 2007/0219464 to Davis et al. Specifically, the Davis et al. reference teaches a steerable guidewire having a sharpened re-entry tip. The guidewire comprises a hypotube having a helical coil attached to and extending from a distal end of the hypotube. A retaining ribbon is connected to the distal end of the hypotube and is also connected to the sharpened re-entry tip. A deflection member is slidably disposed within the hypotube and has a distal end connected to the sharpened re-entry tip such that distal movement of the deflection member deflects the sharpened re-entry tip in one direction, while proximal movement of the deflection member deflects the sharpened re-entry tip in an opposite direction. While the lumen re-entry device of Davis et al. might offer successful deflection of the guidewire tip, the sharpened re-entry tip, which may be used for crossing an occlusion and/or re-entering a vessel lumen, may present risks of inadvertently puncturing or tearing the vessel wall during advancement and/or deflection.

The present disclosure is directed toward one or more of the problems set forth above.

SUMMARY OF THE DISCLOSURE

In one aspect, a lumen re-entry system includes a helically wound coil having an open proximal end and an open distal end and defining a longitudinal movement axis. The helically wound coil includes a relaxed distal segment that is relaxed relative to a proximal segment of the helically wound coil. A tip deflection wire is attached to the relaxed distal segment and coaxially disposed relative to the helically wound coil. Movement of the tip deflection wire in a proximal direction moves the lumen re-entry system from an advancement configuration in which the open distal end of the helically wound coil is substantially aligned with the longitudinal movement axis to a deflected configuration in which the open distal end of the helically wound coil is deflected relative to the longitudinal movement axis. The lumen re-entry system also includes a puncture wire slidably received within the helically wound coil and having a distal puncture tip.

In another aspect, a method of re-entering a lumen of a patient vessel using a lumen re-entry system includes advancing a helically wound coil through a wall of the patient vessel with an open distal end of the helically wound coil substantially aligned with a longitudinal movement axis. An open distal tip of the helically wound coil is deflected relative to the longitudinal movement axis and toward the lumen by moving a tip deflection wire, which is attached to a relaxed distal segment of the helically wound coil, in a proximal direction. The lumen is entered by advancing the puncture wire distally beyond the open distal end of the helically wound coil and penetrating the wall using a distal puncture tip of the puncture wire.

BRIEF DESCRIPTION OF THE DRAWINGS

FIG. 1 is a sectioned side diagrammatic view of a lumen re-entry system, according to one embodiment of the present disclosure;

FIG. 2 is a sectioned side diagrammatic view of an alternative helically wound coil for the lumen re-entry system of FIG. 1 shown in an advancement configuration;

FIG. 3 is a sectioned side diagrammatic view of yet an alternative helically wound coil for the lumen re-entry system of FIG. 1 shown in a deflected configuration;

DETAILED DESCRIPTION

Figure 4:
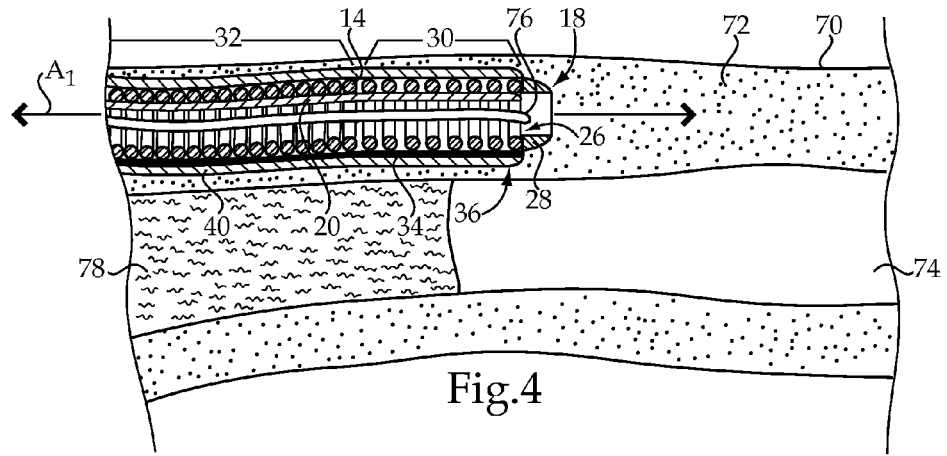
FIG. 4 is a side diagrammatic view of a vascular structure of a patient at one stage of a lumen re-entry procedure using the lumen re-entry system of FIG. 1.

Referring to FIG. 1, there is shown a lumen re-entry system 10 according to one embodiment of the present disclosure. The lumen re-entry system 10 may include a number of components, which may be provided within a sterile, tear open package 12, as is known in the art. In performing a lumen re-entry procedure on a patient, some or all of the components of the lumen re-entry system 10 may be used, depending upon the specifics of the procedure to be performed. As should be appreciated, however, the components shown in FIG. 1 might be separately packaged and/or the lumen re-entry system 10 might also include components in addition to those shown, including components routinely used in percutaneous vascular procedures.

The lumen re-entry system 10 generally includes a helically wound coil 14 having an open proximal end 16 and an open distal end 18. The helically would coil 14, which defines a longitudinal movement axis $A_1$, may be made from stainless steel wire, or other similar material, and may be wound from a material having a circular, or non-circular, cross sectional shape. The helically wound coil 14 may be provided in any desired length and may have any outer diameter, suitable for the intended use of the coil 14. According to some embodiments, mandrel 20 may be positioned within the helically wound coil 14 and, as shown, may extend a majority of a length of the coil 14. The mandrel 20 may be formed from stainless steel, or other commonly selected material, to provide increased stiffness of the coil 14. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The mandrel 20, which may be optional, may include a proximal end 22 attached at or near the open proximal end 16 of the helically wound coil 14 at a first weldment 24. The first weldment 24 may be formed using plasma welding or any other well known welding technique. Although welding or soldering may be preferred, it should be appreciated that other means for providing a strong and durable connection are also contemplated, including, the use of adhesives. The mandrel 20 may be attached to the helically wound coil 14 continuously or discontinuously along the length of the helically wound coil 14, including at or near the open distal end 18 of the coil 14. Specifically, for example, a distal end 26 of the mandrel 20 may be secured to the helically wound coil 14 at a second weldment 28. The second weldment 28 may be similar to the first weldment 24 in materials and configuration. Further, both the first weldment 24 and the second weldment 28 may form atraumatic tips of the helically wound coil 14.

The helically wound coil 14 may also include a safety wire, in addition to the mandrel 20 or as an alternative to the mandrel 20, to reduce the possibility of portions of the helically wound coil 14 breaking loose within a patient, should the helically wound coil 14 unravel. The safety wire may be made from a stainless steel wire, or other similar material, and may preferably have a flattened cross-section. The safety wire may extend a majority of a length of the helically wound coil 14 and, according to some embodiments, may have a proximal end attached at the first weldment 24 and a distal end attached at the second weldment 28. However, it should be appreciated that the safety wire may be provided in any desired length and, further, may be attached at any position or positions along the length of the coil 14.

The helically wound coil 14 includes a relaxed distal segment 30 that is relaxed relative to a proximal segment 32 of the coil 14. As shown, the proximal segment 32 may represent a majority of the length of the helically wound coil 14 while the relaxed distal segment 30 may represent a relatively short distal segment of the coil 14, such as, for example, the distal 2 to 8 centimeters of the coil 14. The coil turns of the relaxed distal segment 30 may be stretched in a well known manner to relax the distal turns, such that the relaxed distal segment 30 provides increased flexibility toward the open distal end 18 of the coil 14. The relaxed distal coil turns also provide a more atraumatic distal tip for the helically wound coil 14.

A tip deflection wire 34 is attached to the relaxed distal segment 30, such as at the second weldment 28, and is coaxially disposed relative to the helically wound coil 14. According to the exemplary embodiment, the tip deflection wire 34 has a distal end 36 connected with the helically wound coil 14 at the second weldment 28, with a length of the wire 34 extending outside the helically wound coil 14. Although specific attachment means are provided, it should be appreciated that any attachment means may be used to permanently or temporarily connect end 36 of the tip deflection wire 34 to the helically wound coil 14. As shown, a proximal end 38 of the tip deflection wire 34 may extend proximally beyond the open proximal end 16 of the helically wound coil 14 and may be used by a clinician to manipulate the relaxed distal segment 30, as will be discussed below. According to embodiments incorporating a mandrel 20, it is preferred that the tip deflection wire 34 and mandrel 20 be positioned on opposite sides of the helically wound coil 14, as shown.

The tip deflection wire 34, according to some embodiments, may include a flexible thread comprising any fiber or combination of fibers, such as, for example, polyester, silk, or cotton. According to alternative embodiments, however, the tip deflection wire 34 may include a metallic material. It should be appreciated that the composition of tip deflection wire 34 may be selected to achieve a desired size or fineness, strength, and elasticity, based on the use of wire 34 with respect to the helically wound coil 14. As stated above, such use will be described below in greater detail.

According to some embodiments, a lubricious polymer coating 40 may surround the helically wound coil 14. The lubricious polymer coating 40, which may include, for example, Teflon, may facilitate smooth movement of the helically wound coil 14 within a vascular structure of a patient. The lubricious polymer coating 40 may extend from the open proximal end 16 to the open distal end 18 of the helically wound coil 14 and may terminate at or near the weldments 24 and 28, as shown in FIG. 1. According to some embodiments, the lubricious polymer coating 40 may be heat shrunk over the helically wound coil 14.

The lumen re-entry system 10 also includes a puncture wire 42 that may be slidably received within the helically wound coil 14, as will be discussed below, and has a distal puncture tip 44. Generally speaking, the puncture wire 42 may be similar to a conventional wire guide and, thus, may include an elongate flexible body 46 extending from a proximal end 48 to a distal end 50. The elongate flexible body 46 is adapted and sized to be inserted through the helically wound coil 14. According to some embodiments, the puncture wire 42 may be made from a metallic material, such as stainless steel, or, alternatively, may be made from a common medical tube material, such as, for example, polytetrafluoroethylene (PTFE), high density polyethylene (HDPE), nylon, polyetheretherketone (PEEK), or any vinyl, plastic, rubber, or silicone. It is desirable for the puncture wire 42 to exhibit both stiffness, or firmness, and flexibility.

For example, the puncture wire 42 should be flexible enough to navigate through the lumen defined by the helically wound coil 14, but stiff enough to provide sufficient force for puncturing through a vasculature wall using the distal puncture tip 44.

The puncture wire 42 may include any of a variety of known configurations. For example, the puncture wire 42 may include an elongate core element with one or more tapered sections near a distal end thereof. According to all embodiments, however, the elongate flexible body 46 terminates in the distal puncture tip 44, which is configured to puncture through a vasculature wall. Specifically, the distal puncture tip 44 may include a sharp needlepoint that points generally along a longitudinal axis of the elongate flexible body 46. The puncture wire 42 may also include a coating, such as a lubricious polymer coating, to facilitate movement of the puncture wire 42 within the helically wound coil 14. The puncture wire 42 may preferably be longer in length than the helically wound coil 14 to facilitate manipulation of the proximal end 48 of the puncture wire 42 by a clinician.

An alternative embodiment of the helically wound coil 14 is shown generally in FIG. 2. Specifically, the helically wound coil 14 of FIG. 2 is similar to that shown in FIG. 1; however, a length of the tip deflection wire 34 is shown extending through the helically wound coil 14 in FIG. 2. In addition, the lubricious polymer coating 40 is shown in FIG. 2 extending from the open proximal end 16 of the coil 14 and terminating prior to the relaxed distal segment 30. Thus, as should be appreciated, numerous modifications, including materials, dimensions, attachments, and configurations, are contemplated.

The lumen re-entry system 10 or, more specifically, the helically wound coil 14 has an advancement configuration, as shown in FIGS. 1 and 2, in which the open distal end 18 of the coil 14 is substantially aligned with the longitudinal movement axis $A_1$. Movement of the tip deflection wire 34 in a proximal direction moves the lumen re-entry system 10 or, more specifically, the helically wound coil 14 from the advancement configuration of FIGS. 1 and 2 to a deflected configuration. According to the deflected configuration, shown in FIG. 3, the open distal end 18 of the helically wound coil 14 is deflected relative to the longitudinal movement axis $A_1$. For example, the open distal end 18 may be deflected such that the open distal end 18 is aligned with a deflection axis $A_2$. As shown, the deflection axis $A_2$ is oriented at an angle greater than zero with respect to the longitudinal movement axis $A_1$. As is also shown in FIG. 3, a distal segment 60 of the tip deflection wire 34 extends through the helically wound coil 14, while a proximal segment 62 extends outside the helically wound coil 14.

INDUSTRIAL APPLICABILITY

The present disclosure is generally applicable to medical devices for use in percutaneous vascular procedures, or other procedures involving cavities, ducts, or canals of a patient. More specifically, the present disclosure is applicable to systems and methods for treating chronic total occlusion (CTO). Yet further, the present disclosure may be specifically applicable methods for entering the subintimal space of a vessel wall and re-entering the lumen defined by the vessel wall after the occlusion.

Referring to FIGS. 4-9, a percutaneous vascular procedure using the lumen re-entry system 10 of FIG. 1 will be described with reference to a vascular structure 70 of a patient. The vascular structure 70, as should be appreciated, includes a vessel wall 72 defining a lumen 74. Although not shown, a clinician may position a needle, or introducer, through the skin of a patient to gain access to the vascular structure 70. At a first stage of the procedure, a clinician may insert a wire guide 76 through a tube of the introducer and into the vascular structure 70. While attempting to cross an occlusion 78 using the wire guide 76, the clinician may inadvertently, or intentionally, penetrate into the vessel wall 72 or, more specifically, the subintimal space of the vessel wall 72. As shown in FIG. 4, the helically wound coil 14 of the lumen re-entry system 10 may be advanced over the wire guide 76 and used to direct the wire guide 76 back into the lumen 74 beyond the occlusion 78.

Specifically, as shown in FIG. 4, the helically wound coil 14 may be advanced through the wall 72 of the patient vessel 70 with the open distal end 18 substantially aligned with the longitudinal movement axis $A_1$. The helically wound coil 14 may be advanced such that the relaxed distal segment 30, or at least a portion thereof, is advanced beyond the occlusion 78. It should be appreciated that the lubricious polymer coating 40 may assist in reducing friction as the helically wound coil 14 is advanced through the vessel wall 72. Once the helically wound coil 14 is properly positioned, the wire guide 76 may be removed, such as by proximally withdrawing or retracting the wire guide 76. It should be appreciated that radiopaque markers and/or additional components and devices that facilitate imaging assisted advancement may be incorporated into the lumen re-entry system 10 described herein.

Figure 5:
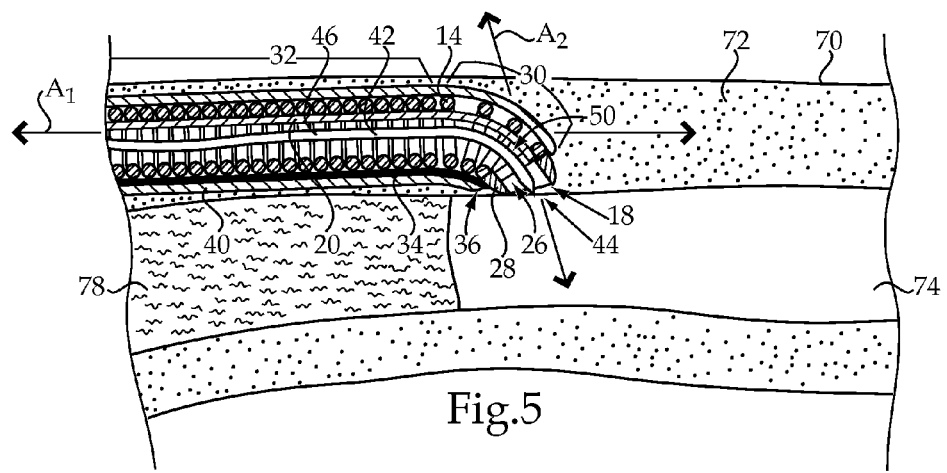
FIG. 5 is a side diagrammatic view of the vascular structure of a patient at another stage of a lumen re-entry procedure using the lumen re-entry system of FIG. 1.

Once the helically wound coil 14 is properly positioned, as described above, the helically wound coil 14 may be moved from the advancement configuration to the deflected configuration, as shown in FIG. 5. Specifically, the open distal end 18 of the helically wound coil 14 may be deflected relative to the longitudinal movement axis $A_1$ and toward the lumen 74 by moving the tip deflection wire 34 in a proximal direction. For example, the open distal end 18 may be deflected such that the open distal end 18 is aligned with a deflection axis $A_2$.

Figure 6:
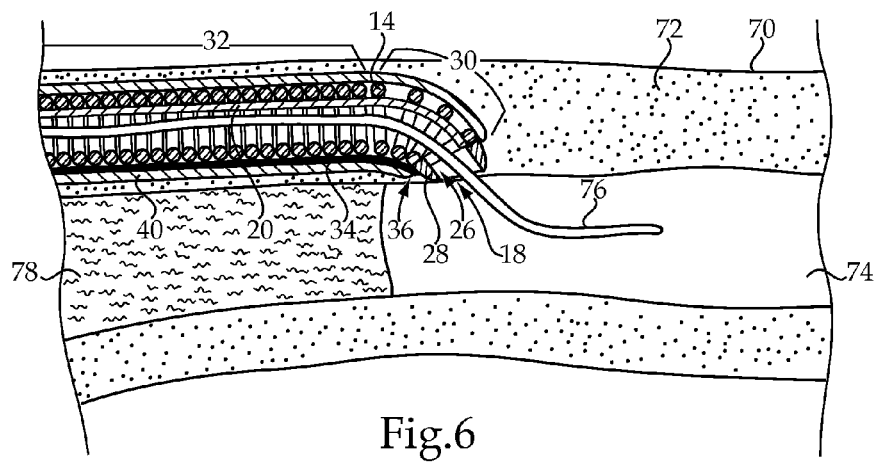
FIG. 6 is a side diagrammatic view of the vascular structure of a patient at another stage of a lumen re-entry procedure using the lumen re-entry system of FIG. 1.

The lumen 74 may then be entered, or re-entered, by advancing the puncture wire 42 through the helically wound coil 14 and distally beyond the open distal end 18, which is in a deflected state, and penetrating the wall 72 using the puncture tip 44. Once the puncture tip 44 has punctured through to the lumen 74, the puncture wire 42 may be removed from the helically wound coil 14 by proximally retracting or withdrawing the puncture wire 42. With the helically wound coil 14 maintained in the deflected configuration, the wire guide 76 may be advanced through the helically wound coil 14, through the puncture in the vessel wall 72 made by the puncture wire 42, and into the lumen 74, as shown in FIG. 6.

Figure 7:
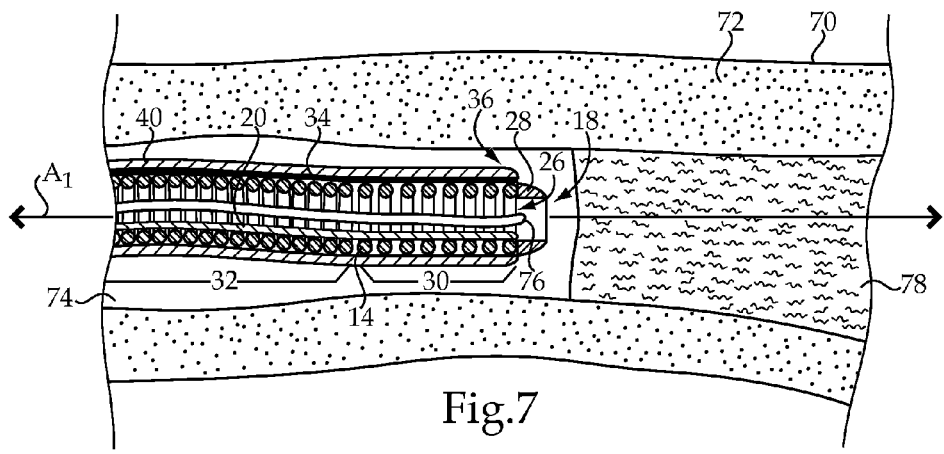
FIG. 7 is a side diagrammatic view of the vascular structure of a patient at one stage of a vessel wall entry procedure using the lumen re-entry system of FIG. 1.
Figure 8:
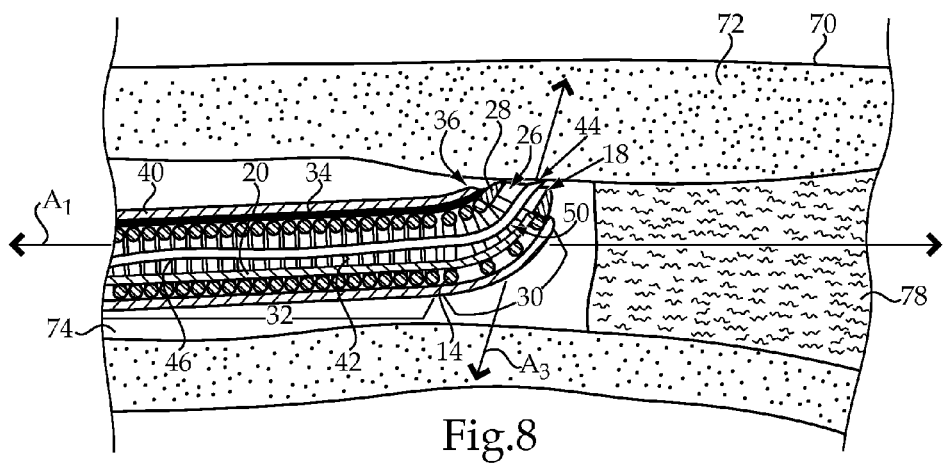
FIG. 8 is a side diagrammatic view of the vascular structure of a patient at another stage of a vessel wall entry procedure using the lumen re-entry system of FIG. 1.

The lumen re-entry system 10 may also be used for intentionally entering the vessel wall 72 from the lumen 74. For example, as shown in FIG. 7, if the wire guide 76 is unsuccessful in crossing the occlusion 78, the helically wound coil 14 may be advanced, in the advancement configuration, through the lumen 74 over the wire guide 76 with the open distal end 18 of the helically wound coil 14 substantially aligned with the longitudinal movement axis $A_1$. With the relaxed distal segment 30 positioned at or near the occlusion 78, the wire guide 76 may be removed and the helically wound coil 14 may be moved from the advancement configuration to the deflected configuration, as shown in FIG. 8. Specifically, the open distal end 18 of the helically wound coil 14 may be deflected relative to the longitudinal movement axis $A_1$ and toward the wall 72 by moving the tip deflection wire 34 in a proximal direction. For example, the open distal end 18 may be deflected such that the open distal end 18 is aligned with a deflection axis $A_3$.

Figure 9:
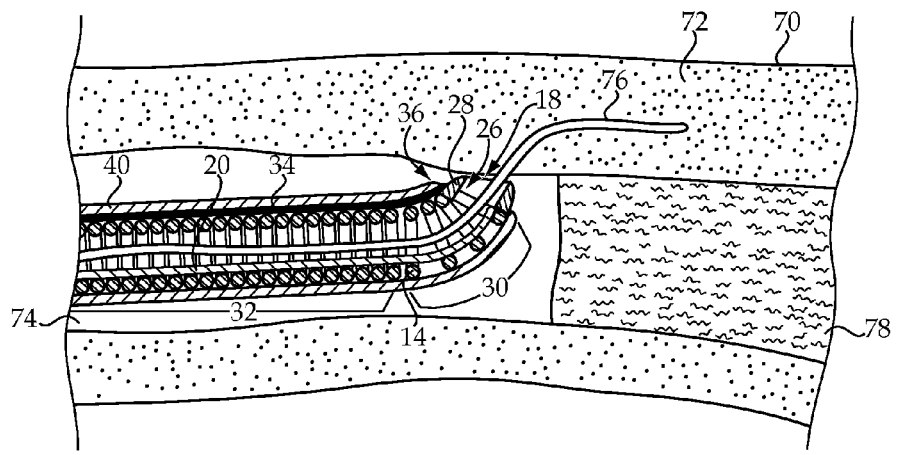
FIG. 9 is a side diagrammatic view of the vascular structure of a patient at another stage of a vessel wall entry procedure using the lumen re-entry system of FIG. 1.

The wall 72 may be entered by advancing the puncture wire 42 through the helically wound coil 14 and distally beyond the open distal end 18, which is in a deflected state, and penetrating the wall 72 using the puncture tip 44. Once the puncture tip 44 has punctured into the wall 72 or, more specifically, the subintimal space of the wall 72, the puncture wire 42 may be removed from the helically wound coil 14 by proximally retracting or withdrawing the puncture wire 42. With the helically wound coil 14 maintained in the deflected configuration, the wire guide 76 may be advanced through the helically wound coil 14, through the puncture in the vessel wall 72 made by the puncture wire 42, and into the wall 72, as shown in FIG. 9.

The lumen re-entry system 10 described herein provides a means for effectively re-entering a patient lumen after a wire guide has inadvertently, or intentionally, advanced into the vessel wall, such as while attempting to cross an occlusion. The puncture wire 42 of the lumen re-entry system 10 is used only when the helically wound coil 14 has been properly positioned and moved into the deflected configuration, thus minimizing the risk of inadvertently puncturing or tearing vessel walls. Further, the hollow helically wound coil 14, having the tip deflection means described herein, may be broadly applicable to a wide variety of percutaneous vascular procedures outside the scope of CTO treatment.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A lumen re-entry system, comprising:
   a helically wound coil having an open proximal end and an open distal end and defining a longitudinal movement axis, wherein the helically wound coil includes a relaxed distal segment that is relaxed relative to a proximal segment of the helically wound coil, and a number of turns per unit length of the helically wound coil in the relaxed distal segment being less than the proximal segment;
   a tip deflection wire attached to the relaxed distal segment and coaxially disposed relative to the helically wound coil, wherein movement of the tip deflection wire in a proximal direction moves the lumen re-entry system from an advancement configuration in which the open distal end of the helically wound coil is substantially aligned with the longitudinal movement axis to a deflected configuration in which the open distal end of the helically wound coil is deflected relative to the longitudinal movement axis; and
   a puncture wire slidably received within the helically wound coil and having a distal puncture tip configured to puncture through a vascular wall.

2. The lumen re-entry system of claim 1, further including a lubricious polymer coating surrounding the helically wound coil.

3. The lumen re-entry system of claim 2, wherein the lubricious polymer coating extends from the open proximal end of the helically wound coil and terminates prior to the relaxed distal segment.

4. The lumen re-entry system of claim 2, wherein a length of the tip deflection wire extends through the helically wound coil from inside to outside of the helically wound coil between adjacent turns thereof.

5. The lumen re-entry system of claim 2, wherein a length of the tip deflection wire extends between an outer surface of the helically wound coil and the lubricious polymer coating.

6. The lumen re-entry system of claim 2, further including a distal weldment securing the tip deflection wire to the relaxed distal segment.

7. The lumen re-entry system of claim 1, wherein the lumen re-entry system includes a puncture configuration in which the open distal end of the helically wound coil is deflected relative to the longitudinal movement axis and the distal puncture tip of the puncture wire is advanced distally beyond the open distal end of the helically wound coil.

8. A method of re-entering a lumen of a patient vessel using a lumen re-entry system, the lumen re-entry system including a helically wound coil having an open proximal end and an open distal end and defining a longitudinal movement axis, wherein the helically wound coil includes a relaxed distal segment that is relaxed relative to a proximal segment of the helically wound coil, and a number of turns per unit length of the helically wound coil in the relaxed distal segment being less than the proximal segment, a tip deflection wire attached to the relaxed distal segment and coaxially disposed relative to the helically wound coil, and a puncture wire slidably received within the helically wound coil and having a distal puncture tip configured to puncture through a vascular wall, the method comprising steps of:
   advancing the helically wound coil through a wall of the patient vessel with the open distal end of the helically wound coil substantially aligned with the longitudinal movement axis;
   deflecting the open distal end of the helically wound coil relative to the longitudinal movement axis and toward the lumen by moving the tip deflection wire in a proximal direction; and
   entering the lumen by advancing the puncture wire distally beyond the open distal end of the helically wound coil and penetrating the wall using the distal puncture tip.

9. The method of claim 8, further including reducing friction during the advancing step by providing a lubricious polymer coating surrounding the helically wound coil.

10. The method of claim 9, wherein the deflecting step includes moving a length of the tip deflection wire through the helically wound coil.

11. The method of claim 9, wherein the deflecting step includes moving a length of the tip deflection wire between an outer surface of the helically wound coil and the lubricious polymer coating.

12. The method of claim 9, further including securing the tip deflection wire to the relaxed distal segment using a distal weldment.

13. The method of claim 8, further including:
   advancing the helically wound coil through the lumen with the open distal end of the helically wound coil substantially aligned with the longitudinal movement axis;
   deflecting the open distal end of the helically wound coil relative to the longitudinal movement axis and toward the wall by moving the tip deflection wire in a proximal direction; and
   entering the wall by advancing the puncture wire distally beyond the open distal end of the helically wound coil and penetrating the wall using the distal puncture tip.

* * * * *